(12) United States Patent
Oberfeld

(10) Patent No.: US 11,273,070 B2
(45) Date of Patent: Mar. 15, 2022

(54) FOOT PROSTHETIC

(71) Applicant: Nina B Oberfeld, Beverly Hills, CA (US)

(72) Inventor: Nina B Oberfeld, Beverly Hills, CA (US)

(*) Notice: Subject to any disclaimer, the term of this patent is extended or adjusted under 35 U.S.C. 154(b) by 513 days.

(21) Appl. No.: 15/918,974

(22) Filed: Mar. 12, 2018

(65) Prior Publication Data

US 2018/0256382 A1 Sep. 13, 2018

Related U.S. Application Data

(60) Provisional application No. 62/470,863, filed on Mar. 13, 2017.

(51) Int. Cl.
*A61F 5/30* (2006.01)
*A61F 13/06* (2006.01)
*A43B 7/22* (2006.01)

(52) U.S. Cl.
CPC .............. *A61F 5/30* (2013.01); *A61F 13/067* (2013.01); *A61F 13/068* (2013.01); *A61F 13/063* (2013.01)

(58) Field of Classification Search
CPC ........ A61F 5/30; A61F 13/063; A61F 13/067; A61F 13/068; A61F 13/064; A43B 7/144; A43B 7/1425; A43B 7/1435; A43B 7/1445
USPC ............................................................ 36/71
See application file for complete search history.

(56) References Cited

U.S. PATENT DOCUMENTS

| 2,120,465 | A | * | 6/1938 | Hartley | ................ A61F 13/063 128/894 |
| 2,221,202 | A | | 11/1940 | Ratcliff | |
| 2,268,777 | A | * | 1/1942 | Scholl | .................... A61F 13/02 128/894 |
| 2,633,129 | A | * | 3/1953 | Crawford | ............. A61F 13/063 602/66 |
| 3,487,832 | A | | 1/1970 | Spence | |
| 3,976,066 | A | | 8/1976 | McCartney | |
| 4,842,931 | A | | 6/1989 | Zook | |
| 5,098,421 | A | | 3/1992 | Zook | |
| 5,109,874 | A | | 5/1992 | Bellingham | |

(Continued)

FOREIGN PATENT DOCUMENTS

| CN | 205337819 U | 6/2016 |
| WO | 2014146212 A1 | 9/2014 |
| WO | 2016007931 A1 | 1/2016 |

OTHER PUBLICATIONS

International Application No. PCT/US18/22050 International Search Report and Written Opinion of the International Searching Authority dated May 21, 2018 (17 Pages).

*Primary Examiner* — Camtu T Nguyen
(74) *Attorney, Agent, or Firm* — Lawrence N. Ginsberg

(57) ABSTRACT

A foot prosthetic having a pressure relieving, weight distribution pad having a convex surface and a concave surface. The pad includes a central portion having a maximum thickness, the pad gradually tapering from the central portion to an outer peripheral edge thereof, the pad providing a cushioning for the foot. An adhesive layer is formed on the concave surface. During use, the concave surface is affixed to a selected portion of the user's foot thus conforming to the unique shape of the selected portion of the user's foot. The gradual tapering provides a smooth transition being formed between the pad and the user's foot at the outer peripheral edge.

20 Claims, 3 Drawing Sheets

(56) References Cited

U.S. PATENT DOCUMENTS

| | | | |
|---|---|---|---|
| 5,497,789 A | 3/1996 | Zook | |
| 6,200,195 B1 | 3/2001 | Furuno et al. | |
| D455,002 S * | 4/2002 | Holden | D2/896 |
| 6,436,020 B1 | 8/2002 | Weingand | |
| 6,506,175 B1 | 1/2003 | Goldstein | |
| 6,598,321 B2 | 7/2003 | Crane et al. | |
| 6,640,465 B1 | 11/2003 | Burgess | |
| 6,641,550 B1 | 11/2003 | Johnson | |
| 6,857,935 B1 | 2/2005 | Dohan | |
| 6,865,759 B2 | 3/2005 | Pearce | |
| 7,087,806 B2 | 8/2006 | Scheinberg et al. | |
| 7,140,126 B2 | 11/2006 | Crane et al. | |
| 7,152,606 B1 | 12/2006 | Schindler | |
| 7,159,342 B2 | 1/2007 | Grisoni et al. | |
| 7,193,002 B2 | 3/2007 | Chen | |
| 7,506,459 B2 | 3/2009 | Grisoni et al. | |
| 7,727,608 B2 | 6/2010 | Cunningham | |
| 7,847,143 B2 * | 12/2010 | Moramarco | A43B 7/1445 602/41 |
| 8,038,660 B2 | 10/2011 | Bruce et al. | |
| 8,296,969 B2 | 10/2012 | Granger et al. | |
| 8,647,169 B2 | 2/2014 | Chang | |
| 8,715,211 B1 | 5/2014 | Prandini | |
| 8,814,818 B2 | 8/2014 | Bushby | |
| D758,058 S | 6/2016 | Granger et al. | |
| D761,543 S | 7/2016 | Granger et al. | |
| D762,366 S | 8/2016 | Granger et al. | |
| D762,367 S | 8/2016 | Granger et al. | |
| D762,368 S | 8/2016 | Granger et al. | |
| D766,560 S | 9/2016 | Granger et al. | |
| 9,439,810 B2 * | 9/2016 | Stilwell | A61F 13/067 |
| D771,921 S | 11/2016 | Granger et al. | |
| 9,492,304 B2 * | 11/2016 | Fontaine | A61F 5/019 |
| 2002/0128580 A1 | 9/2002 | Carlson et al. | |
| 2005/0240139 A1 | 10/2005 | Bushby | |
| 2005/0266059 A1 | 12/2005 | Poss | |
| 2006/0053664 A1 | 3/2006 | Tager | |
| 2008/0250669 A1 | 10/2008 | Hallivis et al. | |
| 2009/0038973 A1 | 2/2009 | Feldman | |
| 2010/0050322 A1 | 3/2010 | Zagula | |
| 2011/0171880 A1 | 7/2011 | Nam | |
| 2011/0225847 A1 * | 9/2011 | Buchanan | A43B 13/026 36/96 |
| 2011/0232129 A1 | 9/2011 | Roberts et al. | |
| 2012/0066815 A1 | 3/2012 | Feeman-Fick | |
| 2012/0227161 A1 | 9/2012 | Canci | |
| 2013/0291410 A1 | 11/2013 | Trauner | |
| 2013/0333242 A1 | 12/2013 | Whiting | |
| 2014/0090273 A1 | 4/2014 | Piontkowski | |
| 2016/0354224 A1 * | 12/2016 | Bushby | A61F 5/0111 |

* cited by examiner

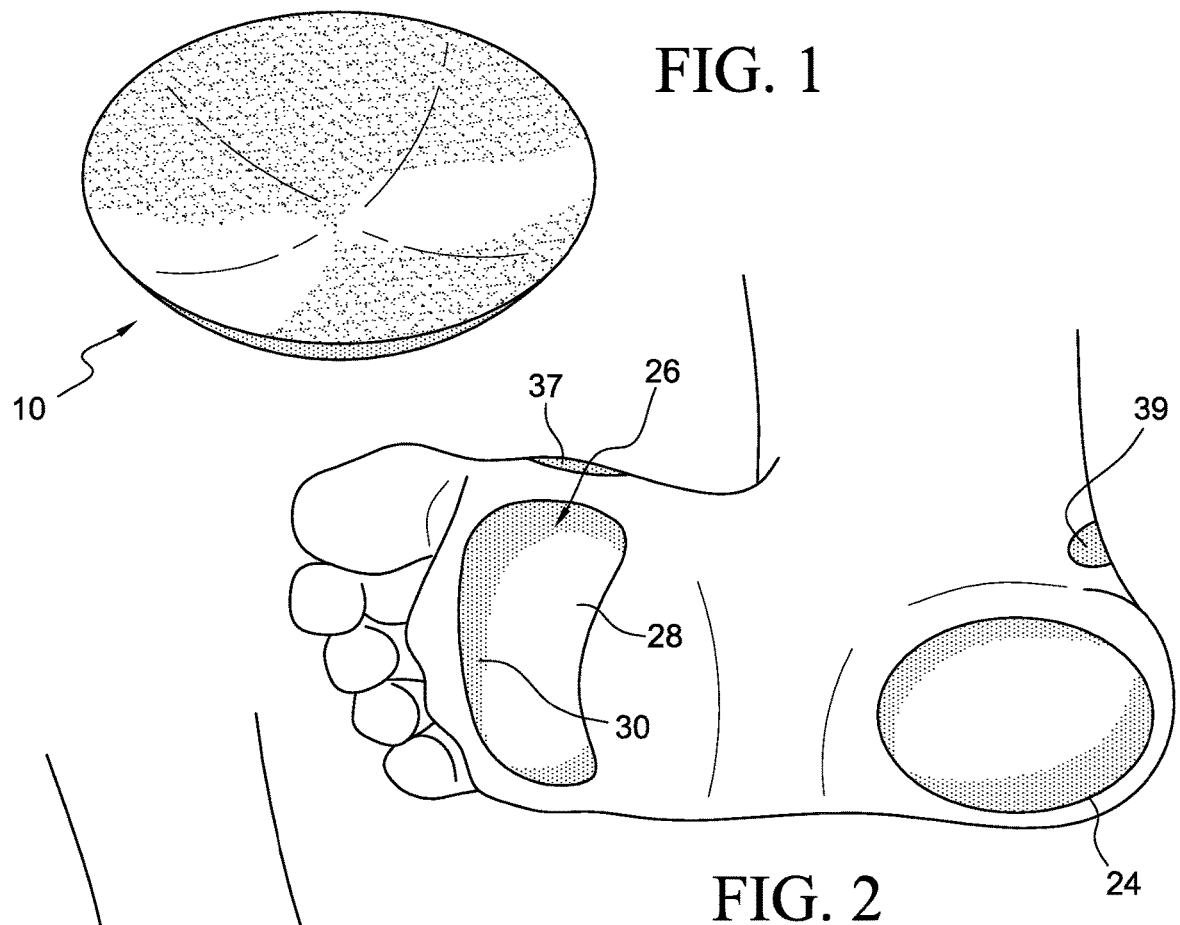
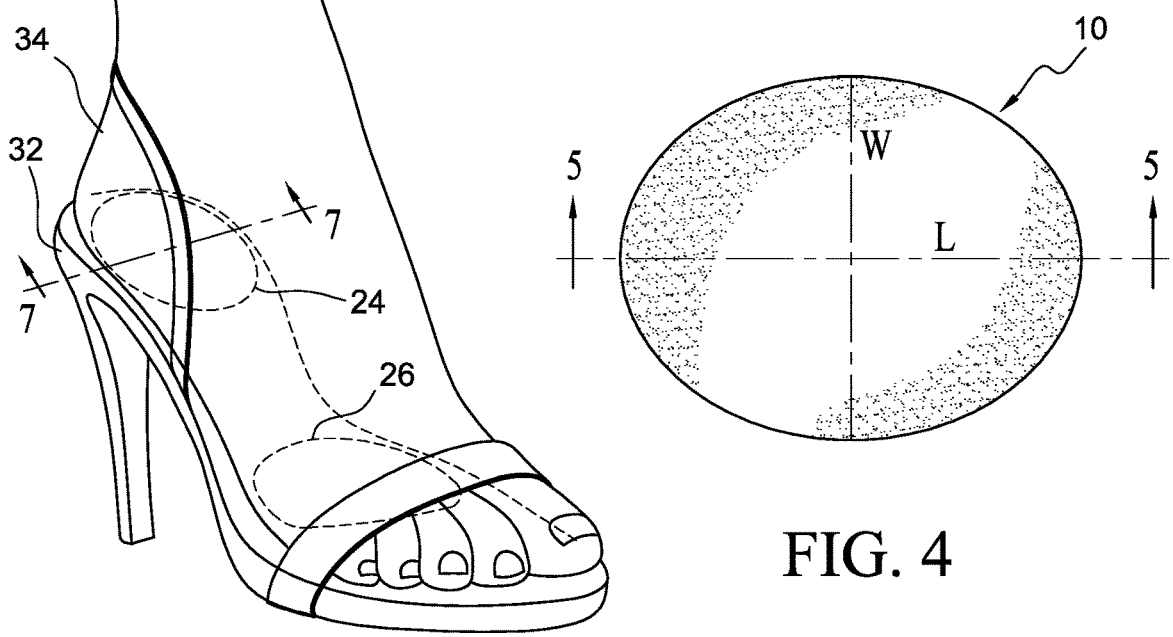

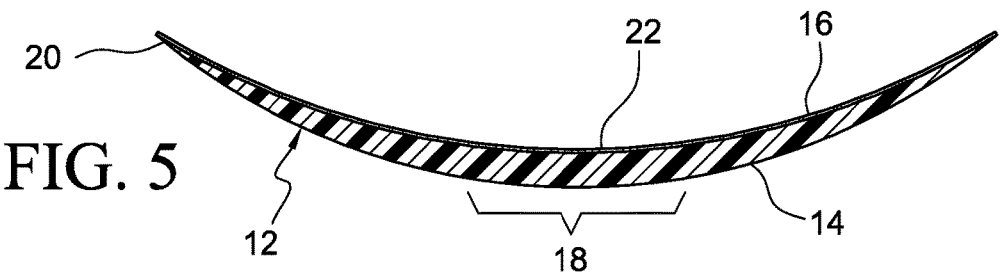
FIG. 5
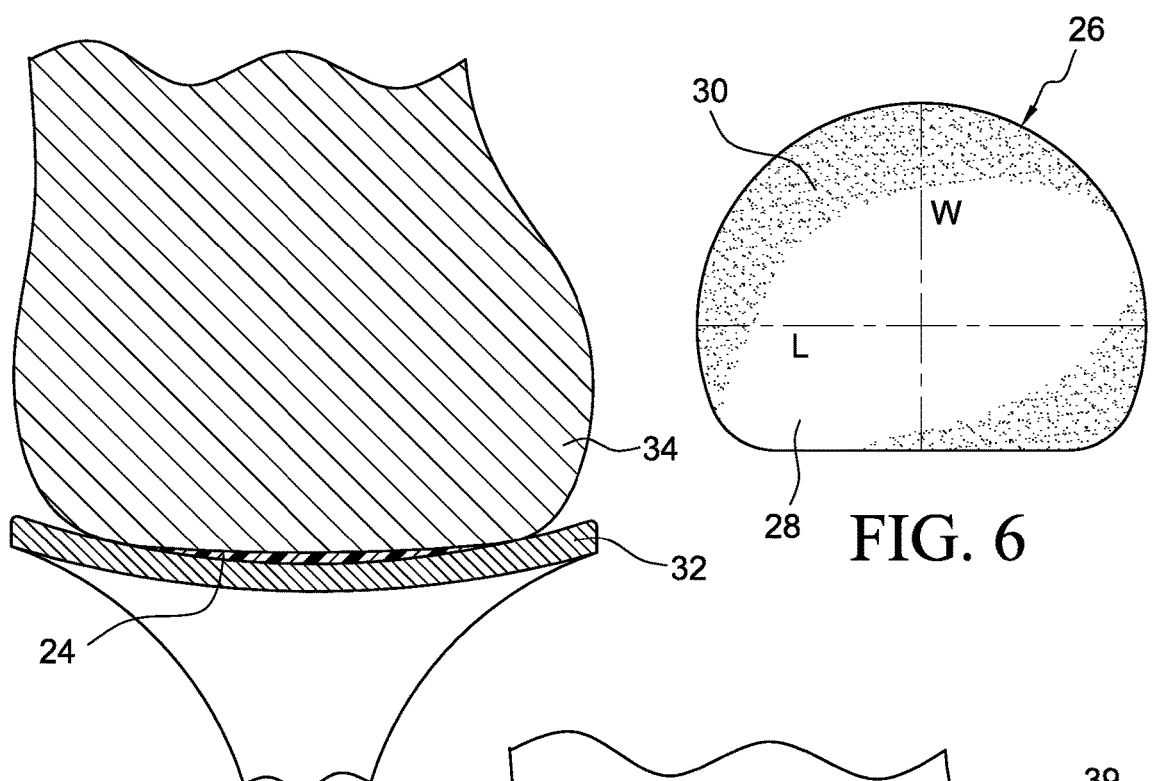
FIG. 6
FIG. 7
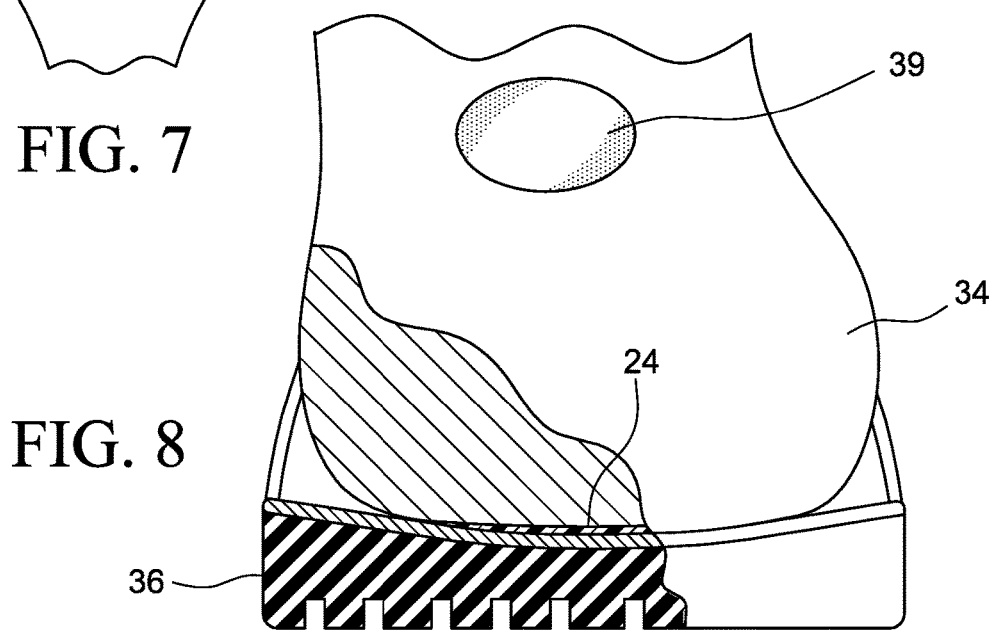
FIG. 8

FOOT PROSTHETIC

CROSS REFERENCE TO RELATED APPLICATIONS

The present application claims benefit of U.S. Provisional Application. No. 62/470,863 filed Mar. 13, 2017, entitled FOOT PROSTHETIC, the entire contents of which are hereby incorporated by reference.

BACKGROUND OF THE INVENTION

1. Field of the Invention

The present invention relates generally to the field of prosthetic devices, and more particularly to a new, uniquely shaped and attractive device and method for relieving foot pain, which is especially adapted to replace the need to use a shoe insert, pressure relieving pads, friction relieving pads, or comfort pads and conceals the fact that the individual suffers from foot pain by wearing this discreet prosthetic, which is simple in construction and consequently economical to manufacture.

2. Description of the Related Art

Both men and women often choose to wear shoe inserts to provide extra cushioning for their feet while using shoes for the effect of relieving moderate pressure on the feet provided by the shoe. Shoe inserts have been designed to be placed in the shoe to provide cushioning. There are times, however, when the use of a shoe insert or insole is impractical, undesirable or impossible. In the summertime, for example sandals and flip flops are often worn, and a shoe insert cannot be placed on a flip flop without slipping off. Some inserts have been designed to have adhesive backing to adhere to the shoe; however, these present an unsightly appearance when the individual walks and the heel lifts upward and separates from the shoe, making the insole visible. Use of an insole or shoe insert is clear evidence that the user suffers from foot pain. Modest and proud people often prefer to wear closed shoes to hide the inserts and avoid admitting their weakness, aging body, foot defect or disability. Even inserts such as those manufactured by Dr. Scholls, Memphis, Tenn., have a bulky appearance, may slip and may damage the lining of the shoe.

Self-adhesive insoles or inserts may leave a sticky reside on the interior of the shoe that will continue to attract dirt and turn dark, or may damage the lining of the shoe when removed.

Non-adhesive pressure relieving foot pads that wrap around the toe or wrap around the foot with straps, are unsightly, provide pressure on the toe or foot, and cannot be discreetly used with open toe shoes because the straps wrap around a toe or foot and can be seen. They can only properly be used with closed toed shoes. Furthermore, when straps wrap around the toe or foot, there is an increase in friction between the pad, toe and the shoe. Additionally, the strap takes up space between the toes thus making the shoebox tighter. This can potentially cause toe pain or numbness.

Adhesive pressure relieving pads, used for metatarsal or bunion pain are flat, do not conform to the unique shape of the user's foot, do not taper to a thin edge, are bulky and do not provide discreet protection.

As will be disclosed below, the present invention is a new, disposable and reusable viable solution enabling people to relieve foot pain discreetly.

Further, as will be disclosed below, the present invention is a new viable solution enabling men, women or children wanting to wear open toed sandals or flip flops to wear these types of shoes and still receive cushioned relief.

At the same time, there are many people that desire to start their day and walk on hard surfaces without using an insert or soft comfortable shoes. Walking on hard surfaces causes inflammation and aggravation to the sensitive spots on their feet and they often endure pain for the rest of the day or even longer. For those individuals, the disposable and reusable prosthetic device of the present invention is an outstanding solution, because it can be removed at night before getting into bed, placed on the bedside table at night and replaced on the foot in the morning before taking a step.

There are those that do not want to dispense with the idea of wearing a soft shoe that will help prevent or alleviate foot pain. Therefore, many people opt for rubber-soled shoes. This is because a soft rubber sole provides a certain level of comfort, modesty and privacy when worn. However, the notion of privacy of foot pain is lost when a person wears big chunky non-fashionable or orthopedic looking rubber soled shoes.

A shoe insert or pad will show when used with open high-heeled sandals and is likely to be visible. For many women, wearing a visible insert or pad is simply not an acceptable alternative. Women who choose not to use inserts or pads with high heels are usually knowingly subjecting themselves to pain. For that reason, many women refuse to wear high heels unless it is necessary or it is for a very important party or meeting.

As will be disclosed below, the foot prosthetic of the present invention enables and empowers users to comfortably wear whatever shoes they desire or even go barefoot with the device attached to their foot, including any bunion, or toe.

SUMMARY OF THE INVENTION

In a broad aspect, the present invention is embodied as a foot prosthetic having a pressure relieving, weight distribution pad having a convex surface and a concave surface. The pad includes a central portion having a maximum thickness, the pad gradually tapering from the central portion to an outer peripheral edge thereof, the pad providing a cushioning for the foot. An adhesive layer is formed on the concave surface. During use, the concave surface is affixed to a selected portion of the user's foot thus conforming to the unique shape of the selected portion of the user's foot. The gradual tapering provides a smooth transition being formed between the pad and the user's foot at the outer peripheral edge.

The prior art neither teaches nor suggests the specialized tapered design or pad of the present invention for the foot which minimizes any sensation of using an insole, insert or pad because it substantially eliminates feeling the edge of the device. The edge of the device is strategically placed by the user so that it does not lay in the ball of the forefoot or the heel. The thick portion of the device is placed over the area where the user feels the greatest sense of pain or their sensitive area. The thin tapered edge of the soft gel-like pad enables it to seamlessly attach to the foot and be less noticeable. By using this product the user is able to apply it and forget about it. Their mind can then focus on daily activities rather than on their foot pain or on adjusting slipping inserts or pads.

The present invention provides a prosthetic device which is intended to overcome the limitations of the prior art. In particular, the present invention provides a foot pad that is easy to manufacture and use. As used herein the word foot is broadly defined to include the toes and any bunions. The foot pad provides an effective means of covering a portion of the forefoot, heel, or any other area of the foot, so that the foot is cushioned and not exposed to the harsh impacts felt by walking or wearing shoes. The present invention can therefore be used in instances where the use of a shoe insert, shoe insole, padded sock, or adhesive bandage or pad is not practical. The foot pad is also an improvement over the use of an insole, shoe insert or pad because it is smaller in size and bulk. It also lacks the use of straps which can cause discomfort. It also lacks thick edges which can cause discomfort. The present invention is therefore more comfortable and easier to wear. The present invention may also be worn without shoes.

Other objects, advantages, and novel features will become apparent from the following detailed description of the invention when considered in conjunction with the accompanying drawings.

BRIEF DESCRIPTION OF THE DRAWINGS

FIG. 1 is top, side perspective view of a first embodiment of the foot prosthetic of the present invention revealing the adhesive layer.

FIG. 2 is a bottom perspective view of a foot with two prosthetics shown attached thereto.

FIG. 3 is a perspective view of a user's foot secured within a high heel shoe, with two foot prosthetics, shown in phantom lines, secured to the foot.

FIG. 4 is a top plan view of an embodiment of the foot prosthetic having a generally circular or oval shape.

FIG. 5 is a section taken along line 5-5 of FIG. 4.

FIG. 6 is a top plan view of another embodiment of the foot prosthetic, particularly useful for the ball of the foot.

FIG. 7 is a view taken along line 7-7 of FIG. 3.

FIG. 8 is a partial section of a foot, a foot prosthetic, and a sandal-type shoe.

The same elements or parts throughout the figures of the drawings are designated by the same reference characters, while equivalent elements bear a prime designation.

DETAILED DESCRIPTION OF THE INVENTION

Figure 9:
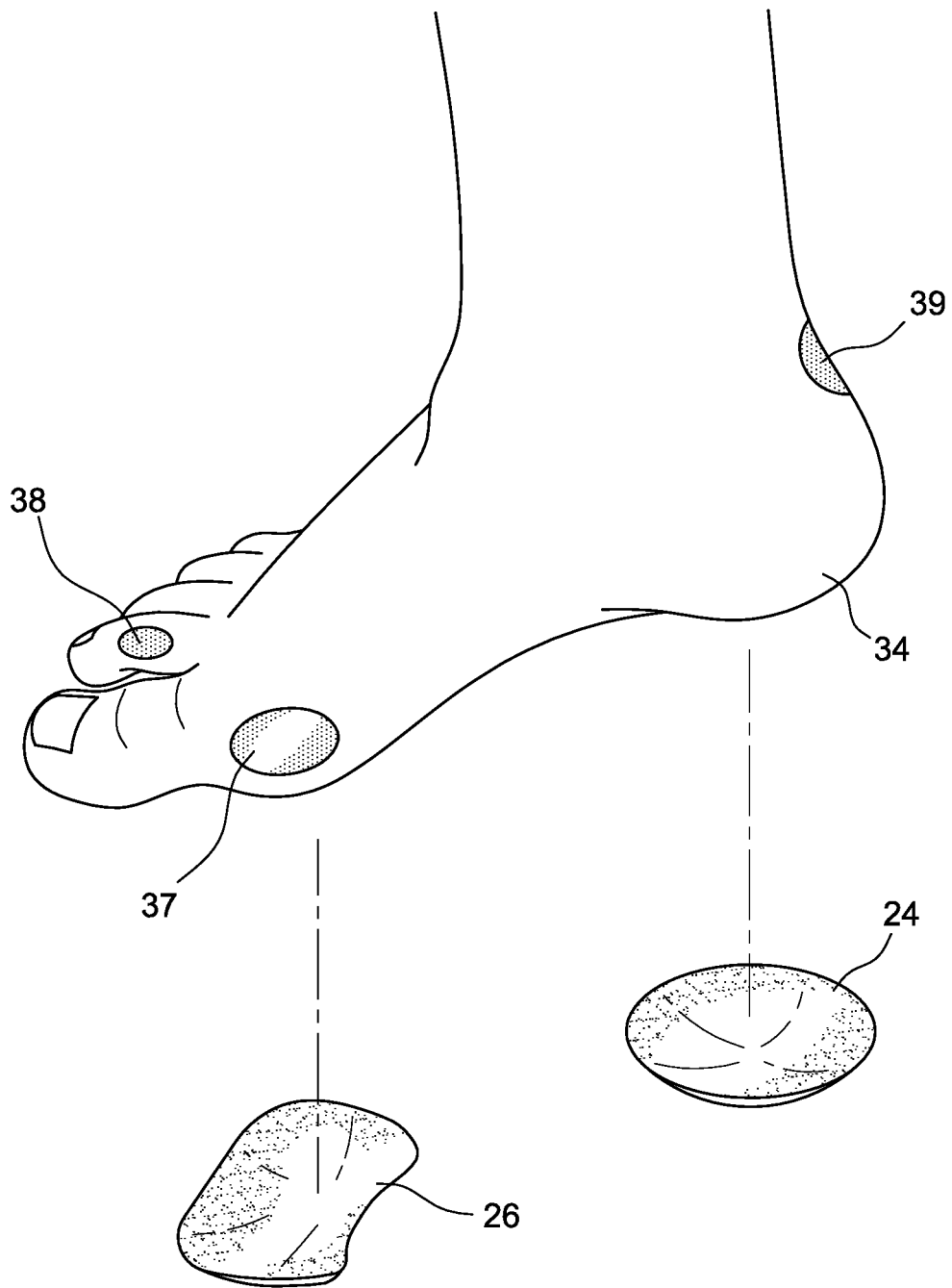
FIG. 9 is an exploded perspective view of a foot with five foot prosthetics shown being attached thereto.

Referring now to the drawings and the characters of reference marked thereon, FIG. 1 illustrates a first embodiment of the foot prosthetic, designated generally as 10, which is typically affixed to the heel of the user's foot. As will be disclosed below in more detail, FIG. 2 shows a foot prosthetic used at the heel, ball of the foot, side bunion area, and ankle. FIG. 3 shows use with high heels, and a top plan view is shown in FIG. 4.

As can be seen in FIG. 5, each foot prosthetic includes a pressure relieving, weight distribution pad 12. The weight distribution pad 12 includes a convex surface 14 and a concave surface. A central portion 18 of the pad 12 has a maximum thickness. The maximum thickness is in a range of between 2 and 6 mm preferably about 4 mm. The pad is made of a single layer soft gel-like material, which provides cushioning, absorbs shock and distributes weight. The pad gradually tapers from the central portion 18 to an outer peripheral edge 20 of the pad 12, the pad 12 providing a cushioning for the foot. The outer peripheral edge preferably has a thickness of 0.01 mm to 0.25 mm. An adhesive layer 22 is formed on the concave surface. During use, a concave surface 16 of the adhesive layer 22 is affixed to a selected portion of the user's foot, thus conforming to the unique shape of the selected portion of the user's foot. The gradual tapering provides a smooth transition being formed between the pad 12 and the user's foot at the outer peripheral edge 20. As can be seen in FIGS. 2 and 3, the pads are configured not to wrap around the edge or side portion of the foot. The foot prosthetic 26 at the ball of the foot is configured to cover the five metatarsal phalangeal joints.

Referring back now to FIGS. 1 and 4, in the first embodiment the foot prosthetic 10 and its associated pressure relieving, weight distribution pad has a generally circular shape. In other embodiments, such as shown in FIG. 2, the foot prosthetic 24 and its associated pressure relieving, weight distribution pad may have a generally oblong shape. A foot prosthetic 26 which is used on the ball of the foot may have main portion 30 with a truncated side portion 28. Such a foot prosthetic 26 is also shown in FIG. 6. In some embodiments, the foot prosthetic may have a generally bean-type shape.

As can be seen in FIG. 3, the set of foot prosthesis shown in FIG. 2, comprising foot prosthetic 24 and foot prosthetic 26 may be utilized with high heel shoes, as shown by numeral designation 32.

The pressure relieving, weight pad of the various embodiments is preferably formed of a gel material such as a silicone gel material or other soft rubber material. Preferably, a soft, low durometer material is utilized to provide the cushioning and support. Thus, as shown in FIG. 7, the prosthetic 24 provides protection for the heel 34. As can be shown, for example in FIG. 8, similar heel protection can be provided regardless of the type of shoes that the user is utilizing. FIG. 8 shows use with a sandal, 36. The present invention is even useful if the user is walking barefoot.

Thus, referring now to FIG. 9, in a method for relieving foot pain, a foot prosthetic or set of foot prosthesis 24, 26, 37, 38, 39 are provided. Each foot prosthetic includes a pressure relieving, weight distribution pad having a convex surface and a concave surface. The pad includes a central portion having a maximum thickness. The pad gradually tapers from the central portion to an outer peripheral edge thereof. An adhesive layer is formed on the concave surface. The foot prosthetic is affixed to a selected portion of a foot of the user. During use the concave surface is affixed to the selected portion thus conforming to a unique shape of the selected portion of the foot. The gradual tapering provides a smooth transition between the foot and the pad at the outer peripheral edge.

In an embodiment of the foot prosthetic having a generally circular shape (i.e. FIG. 1 and FIG. 4), a large size may have a peripheral edge to opposite peripheral edge distance of about 3 inches. A small size for this type of the embodiment may be about 0.5 inches from peripheral edge to opposite peripheral edge. A medium size may be about 2 inches.

A pad has a unique shape and curvature designed to resemble and replicate the shape of the bailor metatarsal portion of the foot. Foot prosthetic has the form and function to help the device seamlessly adhere to the ball of the foot, enabling the device to be concealed under ball of the foot when the user is using the device with flip flops, sandals, high heels or any other open shoes. When the user's foot lifts upward and separates from the open flip flop the prosthetic shown in FIG. 6 is concealed under the ball of the foot. The shape of the prosthetic in FIG. 6, along with the convex and concave design of this prosthetic device enables this new foot prosthetic to provide comfort and reduce pain without anyone else knowing the user is using a pad.

Forefoot Pad (Units in Inches)

|  | W | L |
| --- | --- | --- |
| Small | 1.5 | 2.5 |
| Med | 1.75 | 2.5 |
| Large | 2.0 | 2.75 |
| Xlarge | 3.0 | 3.0 |

An embodiment of the foot prosthetic having the oblong bean type shape (i.e. numeral designation 26 in FIG. 6) is best suited for the forefoot. The dimension W, has a preferred range of between about 1.5 inches to 3.0 inches, and the dimension L, has a preferred edge range of about 2.5 inches to 3.0 inches. Users will purchase the size that best correlates to their foot size.

In an embodiment of the foot prosthetic an oval type shape is preferable for the heel, bunion, and toe portion of the foot. The dimension W, in FIG. 4, would have a preferred range of between about 0.5 inches to 2.75 inches, and the dimension L, would have a preferred edge in the range of 0.5 inches to 2.75 inches. Users will purchase the size that best correlates to their foot size, or pressure sensitive area.

In one embodiment of the foot prosthetic having the oval shape, (i.e. FIG. 2, numeral designation 24), is preferable for use on the heel portion of the foot. This is preferably different sizes to fit multiple sizes of feet. Preferably the user will choose a size sufficient to adhere to the bottom of the heel without excess pad going up the side of the heel. The smaller size oval pads enable the pad to form to bottom of the foot in a discreet way and are not visible from the side view of the foot. Users with larger feet will preferably use the larger pad to provide cushioning to a larger area of their foot. People with small feet may prefer to use the larger pad when using closed shoes such as loafers since it will provide coverage, more comfort, more cushioning and more pain relief. A small oval pad, with its unique design may be placed by the user on any area of the foot, including the forefoot side, or toe. This oval shape can be used on any area if the user desires a small pad that provides comfort and relieves pressure.

Heel Pad (Units in Inches)

|  | W | L |
| --- | --- | --- |
| Small | 0.5 | 1.0 |
| Med | 1.0 | 1.5 |
| Large | 2.0 | 2.5 |
| Xlarge | 2.75 | 2.75 |

As can be seen in, for example, FIG. 9, different embodiments of the foot prosthetic of the present invention can be used with various portions of the foot including the toe, bunion and back of the heel as shown by numeral designations 37, 38 and 39. They have preferably different sizes to fit multiple sizes of problem areas of feet. Preferably the user will choose a size sufficient to adhere to the painful area without excess pad going up the side of the foot. The smaller size oblong pads enable the pad to form to any portion of the foot in a discreet way and are not visible from the side view of the foot. Users with bunions or neuromas will preferably use the smaller pads to provide cushioning to particular problem areas of their foot. People may prefer to use the pads on the sides of the feet or on top of the toes when using closed shoes such as loafers since the prosthetic will provide coverage, more comfort, more cushioning and more pain relief. A small oblong, oval or circular pad, with its unique design may be placed by the user on any area of the foot, including the toes. These unique shapes can be used on any area the user desires a small discreet pad that provides comfort and relieves pressure. The small pad 38 for the side of the toe may be, for example about 0.5 inches in width and 1 inch in length.

The adhesive is preferably a high tack transdermal adhesive or pressure sensitive adhesive. It is a tacky substance that once applied to the user's foot adheres to the foot preventing the pad from slipping or moving until the user removes it. This self-adhering property provides skin protection, reduces friction and provides general comfort which enables the pad to prevent and relieve pain. It is preferably a washable adhesive making the pad reusable. In one embodiment, the adhesive is applied to the pad during manufacturing. In one embodiment, the adhesive is applied during manufacturing and removed by the user and later reapplied by the user when necessary. In another embodiment, the adhesive is not applied during manufacture but is applied instead by the user.

The present invention typically comes as a kit including packaging including instructions for use. A schematic is provided with an identification of foot prosthetic locations. Instructions typically indicate that the foot should be clean and dry, and the sticky side is placed against the clean and dry foot. The foot prosthetic may be removed, repositioned and reused. It can be washed with cool water and be allowed to air dry. It may be stored in the original case or a cool dry place. The present invention preferably comes up with a thin plastic film which covers and prevents the sticky side from attracting dirt before use. The instructions will indicate that the user should discard the plastic film in order to apply the prosthetic.

The present invention typically and preferably comes in flesh tone colors that resemble skin tone which enable the device to be discreet and unnoticeable.

The present invention, in one of its embodiments, may also be manufactured in clear gel, different colors gels, vibrant colors, or with decorative designs or wording or unique textures. This embodiment may appeal to a user who likes flashy and fun items, yet still wants functional and discreet cushioning and pain relief. Just as some men enjoy wearing dress socks with a design or saying on the lop where nobody else can see it, the user can enjoy wearing this unique prosthetic for comfort and pain relief.

The invention claimed is:
1. A foot prosthetic, comprising:
   a) a pressure relieving, weight distribution pad comprising a single layer having a convex surface and a concave surface, wherein said pressure relieving, weight distribution pad includes a central portion having a maximum thickness, said pressure relieving, weight distribution pad tapering from said central portion to an outer peripheral edge thereof, said pressure relieving, weight distribution pad is adapted to provide cushioning for a user's foot;
   b) an adhesive layer formed on said concave surface, said adhesive layer having a concave surface comprising material configured to attach said pressure relieving, weight distribution pad directly to the user's foot;
   wherein during use the concave surface of the adhesive layer is directly affixed to a selected portion of the user's foot thus conforming to a unique shape of the selected portion of the user's foot, wherein said tapering provides a smooth transition being formed between the pressure relieving, weight distribution pad and the user's foot at said outer peripheral edge, said pressure relieving, weight distribution pad enabling use with or without shoes, wherein said selected portion of the user's foot includes the ball of the foot, wherein said pressure relieving, weight distribution pad has a generally oblong shape with a main portion and a truncated side portion; wherein said adhesive layer comprises a high tack or pressure sensitive adhesive; and, wherein said pressure relieving, weight distribution pad is configured to cover five metatarsal phalangeal joints and configured not to wrap around the edge or side portion of the user's foot.

2. The foot prosthetic of claim 1, wherein said pressure relieving, weight distribution pad has a flesh tone color which enhances the ability to be discreet.

3. The foot prosthetic of claim 1, wherein said pressure relieving, weight distribution pad has a decorative design.

4. The foot prosthetic of claim 1, wherein said maximum thickness is in a range of between 2 and 6 mm.

5. The foot prosthetic of claim 1, wherein a thickness at the outer peripheral edge is in a range of between 0.01 and 0.25 mm.

6. The foot prosthetic of claim 1, wherein said pressure relieving, weight distribution pad is formed of a gel material.

7. The foot prosthetic of claim 1, wherein said pressure relieving, weight distribution pad is formed of a silicone gel material.

8. The foot prosthetic of claim 1, wherein said pressure relieving, weight distribution pad is formed of a soft rubber material.

9. A method for relieving foot pain comprising:
a) providing a first foot prosthetic and a second foot prosthetic each prosthetic, comprising:
a pressure relieving, weight distribution pad having a convex surface and a concave surface, wherein said pressure relieving, weight distribution pad includes a central portion having a maximum thickness, said pressure relieving, weight distribution pad tapering from said central portion to an outer peripheral edge thereof, said pressure relieving, weight distribution pad is adapted to provide cushioning for a user's foot;
an adhesive layer formed on said concave surface, said adhesive layer having a concave surface comprising material configured to attach said pressure relieving, weight distribution pad directly to the user's foot;
b) affixing said first foot prosthetic to a first selected portion of the user's foot including the ball of the foot, wherein during use the concave surface of the adhesive layer is adapted to directly affix to the first selected portion thus conforming to a unique shape of the first selected portion, wherein said tapering provides a smooth transition between the pressure relieving, weight distribution pad and the foot at said outer peripheral edge, said pressure relieving, weight distribution pad enabling use with or without shoes, and wherein said pressure relieving, weight distribution pad of said first foot prosthetic is configured to cover the five metatarsal phalangeal joints and configured not to wrap around the edge or side portion of the user's foot; and
c) affixing said second foot prosthetic to a second selected portion of the user's foot wherein during use the concave surface of the adhesive layer is adapted to directly affix to the second selected portion thus conforming to a unique shape of the second selected portion, wherein said tapering provides a smooth transition between the pressure relieving, weight distribution pad and the foot at said outer peripheral edge, said pressure relieving, weight distribution pad enabling use with or without shoes, and wherein said pressure relieving, weight distribution pad of said second foot prosthetic is configured to cover the heel of the user's foot, wherein one of said foot prosthetics being positioned at a selected portion of the user's foot including the ball of the foot; and the other of the foot prosthetics being positioned at a selected portion of the user's foot including the heel of the foot, thus providing comfort when using shoes or walking barefoot.

10. The method of claim 9, wherein the first foot prosthetic positioned at the ball of the foot has an oblong shape with a main portion and a truncated side portion, the adhesive thereon comprising a high tack or pressure sensitive adhesive.

11. The method of claim 9, wherein the second foot prosthetic positioned at the heel of the foot has a generally oblong shape.

12. A foot prosthetic kit for relieving foot pain, comprising:
a) packaging including instructions for use having a schematic with an identification of foot prosthetic locations;
b) at least one foot prosthetic, comprising:
a pressure relieving, weight distribution pad comprising a single layer having a convex surface and a concave surface, wherein said pressure relieving, weight distribution pad includes a central portion having a maximum thickness, said pressure relieving, weight distribution pad tapering from said central portion to an outer peripheral edge thereof, said pressure relieving, weight distribution pad is adapted to provide cushioning for a user's foot;
an adhesive layer formed on said concave surface, said adhesive layer having a concave surface comprising material configured to attach said pressure relieving, weight distribution pad directly to the user's foot;
wherein during use the concave surface of the adhesive layer is adapted to directly affix to the selected portion thus conforming to a unique shape of the selected portion, wherein said tapering provides a smooth transition between the pressure relieving, weight distribution pad and the foot at said outer peripheral edge, said pressure relieving, weight distribution pad enabling use with or without shoes,
wherein said at least one foot prosthetic includes:
a foot prosthetic for a selected portion of the user's foot including the ball of the foot, wherein said pressure relieving, weight distribution pad has a generally oblong shape with a main portion and a truncated side portion; wherein said adhesive layer comprises a high tack or pressure sensitive adhesive; and, wherein said pressure relieving, weight distribution pad is configured to cover five metatarsal phalangeal joints and configured not to wrap around the edge or side portion of the user's foot.

13. The foot prosthetic kit for relieving foot pain of claim 12, wherein said at least one foot prosthetic kit comprises one or more sets of reusable foot prosthetics, adhesive, cleaning wipes and instructions on how to clean the foot before applying the prosthetic, how to apply and remove the adhesive to the foot prosthetics and where to place the foot prosthetics.

14. The foot prosthetic kit for relieving foot pain of claim 12, wherein said at least one foot prosthetic comprises a set of foot prosthetics, comprising:
   a) a first foot prosthetic configured to be positioned at the ball of the foot; and,
   b) a second foot prosthetic configured to be positioned at the heel of the foot.

15. The foot prosthetic kit for relieving foot pain of claim 12, wherein said at least one foot prosthetic comprises a set of foot prosthetics, each foot prosthetic of said set being the same size, and either foot prosthetic being usable for either forefront or the heel portion of the foot.

16. The foot prosthetic kit for relieving foot pain of claim 12, wherein said at least one foot prosthetic comprises one or more sets of disposable foot prosthetics.

17. The foot prosthetic kit for relieving foot pain of claim 12, wherein said at least one foot prosthetic comprises one or more sizes of reusable foot prosthetics.

18. The foot prosthetic kit for relieving foot pain of claim 12, wherein said at least one foot prosthetic comprises a set of foot prosthetics and adhesive with instructions on how to apply the adhesive to the foot prosthetics, how to remove the adhesive and instructions for placement and use.

19. The foot prosthetic kit for relieving foot pain of claim 12, wherein said at least one foot prosthetic kit comprises one or more sets of reusable foot prosthetics, adhesive, adhesive solvent and instructions on how to apply and remove the adhesive to the foot prosthetics and where to place the foot prosthetics.

20. A method for relieving foot pain, comprising:
a) providing a foot prosthetic, comprising:
   a pressure relieving, weight distribution pad comprising a single layer having a convex surface and a concave surface, wherein said pressure relieving, weight distribution pad includes a central portion having a maximum thickness, said pressure relieving, weight distribution pad tapering from said central portion to an outer peripheral edge thereof, said pressure relieving, weight distribution pad is adapted to provide cushioning for a user's foot;
   an adhesive layer formed on said concave surface, said adhesive layer having a concave surface comprising material configured to attach said pressure relieving, weight distribution pad directly to the user's foot;
b) affixing said foot prosthetic to a selected portion of the user's foot including the ball of the foot, wherein during use the concave surface of the adhesive layer is adapted to directly affix to the selected portion thus conforming to a unique shape of the selected portion, wherein said tapering provides a smooth transition between the pressure relieving, weight distribution pad and the foot at said outer peripheral edge, said pressure relieving, weight distribution pad enabling use with or without shoes, and wherein said pressure relieving, weight distribution pad of said foot prosthetic is configured to cover five metatarsal phalangeal joints and configured not to wrap around the edge or side portion of the user's foot; and
wherein said foot prosthetic is positioned at the ball of the foot, thus providing comfort when using shoes or walking barefoot.

\* \* \* \* \*